United States Patent
Selent et al.

(10) Patent No.: US 8,003,816 B2
(45) Date of Patent: Aug. 23, 2011

(54) BISPHOSPHITE LIGANDS FOR HYDROFORMYLATION CATALYZED BY TRANSITION METALS

(75) Inventors: Detlef Selent, Rostock (DE); Armin Boerner, Rostock (DE); Burkard Kreidler, Recklinghausen (DE); Dieter Hess, Marl (DE); Klaus-Diether Wiese, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 16 days.

(21) Appl. No.: 12/515,967

(22) PCT Filed: Nov. 13, 2007

(86) PCT No.: PCT/EP2007/062248
§ 371 (c)(1), (2), (4) Date: May 22, 2009

(87) PCT Pub. No.: WO2008/071508
PCT Pub. Date: Jun. 19, 2008

(65) Prior Publication Data
US 2010/0036143 A1 Feb. 11, 2010

(30) Foreign Application Priority Data
Dec. 13, 2006 (DE) .......................... 10 2006 058 682

(51) Int. Cl.
C07F 15/04 (2006.01)
C07F 9/02 (2006.01)
C07C 45/50 (2006.01)

(52) U.S. Cl. .............................. 558/78; 556/13; 568/454

(58) Field of Classification Search .................. 568/454; 556/13; 558/78
See application file for complete search history.

(56) References Cited

U.S. PATENT DOCUMENTS

| | | | |
|---|---|---|---|
| 5,179,055 A * | 1/1993 | Wink et al. | 502/166 |
| 5,202,297 A * | 4/1993 | Lorz et al. | 502/166 |
| 5,821,389 A * | 10/1998 | Briggs et al. | 568/454 |
| 6,331,657 B1 | 12/2001 | Kaizik et al. | |
| 6,403,837 B1 | 6/2002 | Hess et al. | |
| 6,555,716 B2 | 4/2003 | Protzmann et al. | |
| 6,570,033 B2 | 5/2003 | Rottger et al. | |
| 6,818,770 B2 | 11/2004 | Selent et al. | |
| 6,855,657 B2 * | 2/2005 | Zhang | 502/166 |
| 6,924,389 B2 | 8/2005 | Jackstell et al. | |
| 6,956,133 B2 | 10/2005 | Jackstell et al. | |
| 7,009,068 B2 | 3/2006 | Schmutzler et al. | |
| 7,161,020 B2 | 1/2007 | Selent et al. | |
| 7,193,116 B2 | 3/2007 | Moeller et al. | |
| 7,217,828 B2 | 5/2007 | Selent et al. | |
| 7,294,729 B2 * | 11/2007 | Peng et al. | 556/12 |
| 7,317,130 B2 | 1/2008 | Moller et al. | |
| 7,345,185 B2 | 3/2008 | Ortmann et al. | |
| 7,361,786 B2 | 4/2008 | Boerner et al. | |
| 7,495,133 B2 | 2/2009 | Borgmann et al. | |
| 7,589,215 B2 | 9/2009 | Boerner et al. | |
| 7,745,666 B2 * | 6/2010 | Sugioka et al. | 568/454 |
| 2003/0144559 A1 | 7/2003 | Hess et al. | |
| 2003/0195368 A1 | 10/2003 | Rottger et al. | |
| 2005/0209455 A1 | 9/2005 | Boerner et al. | |
| 2006/0089469 A1 | 4/2006 | Komarov et al. | |
| 2007/0112219 A1 | 5/2007 | Ortmann et al. | |
| 2007/0149781 A1 | 6/2007 | Riermeier et al. | |
| 2007/0197799 A1 | 8/2007 | Holz et al. | |
| 2008/0200695 A1 | 8/2008 | Holz et al. | |

FOREIGN PATENT DOCUMENTS

| | | |
|---|---|---|
| EP | 0 472 071 | 2/1992 |
| JP | 10130190 | * 5/1998 |
| JP | 11 292887 | 10/1999 |
| JP | 11292887 | * 10/1999 |
| WO | 2007 114445 | 10/2007 |

OTHER PUBLICATIONS

Beghetto et al., {Synthesis of new chiral phosphine-phosphites and diphosphites and their application in asymmetric hydroformylation, Catalysis Communications (2001), 2(3-4), 139-143}.*
Lindsell et al., {Synthesis and characterization of a,w- and a-functionalized hydrogenated polybutadienes: telechelic and semi-telechelic amine and phosphite terminated polymers, Polymer (1997), 38(11), 2835-2848}.*
Fell et al., {Hydrolytic stable ammonium salts of sulfonated organic phosphites and their use as cocatalysts in the rhodium-catalyzed hydroformylation of olefins, Journal fuer Praktische Chemie/Chemiker-Zeitung (1993), 335(1), 75-82.*
U.S. Appl. No. 09/708,646, filed Nov. 9, 2000, Hess, et al.
U.S. Appl. No. 12/373,921, filed Jan. 15, 2009, Hess, et al.
U.S. Appl. No. 12/594,602, filed Oct. 5, 2009, Selent, et al.
U.S. Appl. No. 12/992,032, filed Nov. 10, 2010, Kreidler, et al.
U.S. Appl. No. 12/995,800, filed Dec. 2, 2010, Lueken, et al.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a bisphosphite of the formula I

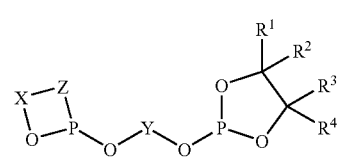

where X=a divalent substituted or unsubstituted bisalkylene or bisarylene radical, Y=a divalent substituted or unsubstituted bisarylene or bisalkylene radical, Z=oxygen or $NR^9$, and $R^1$, $R^2$, $R^3$, $R^4$ are identical or different, substituted or unsubstituted, linked, unlinked or fused aryl or heteroaryl radicals and $R^9$ is hydrogen or a substituted or unsubstituted alkyl or aryl radical, a process for preparing it and also the use of this phosphite in catalysis in particular in the catalytic hydroformylation of olefins or organic compounds having C—C double bonds.

20 Claims, No Drawings

BISPHOSPHITE LIGANDS FOR HYDROFORMYLATION CATALYZED BY TRANSITION METALS

The present invention relates to bisphosphites of the formula I, a process for preparing them and the use of these bisphosphites in catalytic reactions.

The reaction between alkenes (olefins), carbon monoxide and hydrogen in the presence of a catalyst to form aldehydes having one more carbon atom is referred to as hydroformylation (oxo process). Transition metal compounds of Group VIII of the Periodic Table of the Elements, in particular compounds of rhodium and of cobalt, are frequently used as catalysts in these reactions. Hydroformylation using rhodium generally offers the advantage of higher activity and thus usually better economics compared to the use of cobalt catalysts. Complexes comprising rhodium and preferably trivalent phosphorus compounds as ligands are usually used in rhodium-catalysed hydroformylation. Known ligands are, for example, those from the classes of phosphanes (phosphines), phosphinites, phosphonites and phosphites. A good overview of the art in the hydroformylation of olefins may be found in CORNILS, B., HERRMANN, W. A., "*Applied Homogeneous Catalysis with Organometallic Compounds*", Vol. 1&2, VCH, Weinheim, N.Y. 1996 und in WIESE, K.-D., OBST, D., in: Top. *Organomet. Chem.* Vol. 18, Springer Verlag 2006, edited by Matthias Beller, and specifically for rhodium-catalysed hydroformylation: VAN LEEUWEN, P., CLAVER, C. "*Rhodium catalyzed hydroformylation*", Springer 2000 and VAN LEEUWEN, P. "*Homogeneous Catalysis: Understanding the Art*", Springer 2005.

The choice of catalyst system (cobalt or rhodium and suitable ligands) is in each case dependent on the substrate selected and the desired target compound. Some examples are given below:

The most frequently employed ligand is triphenyl-phosphane, if desired in a water-soluble form produced by substitution with polar groups, which has to be used in a large ligand/rhodium ratio in order to hydro-formylate α-olefins with high selectivity to terminal aldehydes, i.e. to n-aldehydes, at comparatively low pressures.

Bisphosphane ligands and their use in the hydroformylation of olefins at low synthesis gas pressures are described, for example, in U.S. Pat. No. 4,694,109 and U.S. Pat. No. 4,879,416. WO 95/30680 discloses the use of bidentate phosphane ligands in catalytic reactions, including hydroformylation reactions. The patent documents U.S. Pat. No. 4,169,861, U.S. Pat. No. 4,201,714 and U.S. Pat. No. 4,193,943 describe ferrocene-bridged bisphosphanes as ligands for hydroformylation.

Monophosphites, too, are suitable ligands for the rhodium-catalysed hydroformylation of branched olefins having internal double bonds, albeit at a low selectivity for the terminally hydroformylated compounds which are normally desired. EP 0 155 508 describes the use of bisarylene-substituted monophosphites in the rhodium-catalysed hydroformylation of sterically hindered olefins, e.g. isobutene.

Rhodium-bisphosphite complexes catalyse the hydroformylation of linear olefins having terminal and internal double bonds to give predominantly terminal aldehydes, but selectivities of greater than 95% are unusual. Such phosphites are generally very hydrolysis-labile. The use of substituted bisaryl diols as starting materials for phosphite ligands produced considerable improvements, as described in EP 0 214 622 or EP 0 472 071.

Frequent secondary or subsequent reactions in the metal-catalysed hydroformylation reaction are hydrogenation, for instance of olefins to alkanes or of aldehydes to alcohols, and isomerization of double bonds. The latter is utilized in EP 1 201 675 and US 2006100453 in order to preferably firstly isomerize internal alkenes to terminal olefins by means of an O-acyl phosphite ligand and then terminally hydro-formylate this, i.e. to form n-aldehydes. EP 0 472 071 describes structurally similar rhodium-bisphosphite catalysts which display high isomerization activities at moderate n-selectivities in the hydroformylation of 2-butene. However, this isomerization reaction is sometimes undesirable since, conversely, terminal olefins also isomerize to internal alkenes, with the latter being the thermodynamically more stable species.

A class of ligands which does not bring about isomerization comprises the phosphabarrelenes described by B. Breit et al. in Chem. Eur. J. 2006, 12, 6930-6939. 2-Octene was converted by means of these into 2-methyloctanal and 2-ethylheptanal with virtually no isomerization and with a regioselectivity of only 62:38. The hydroformylation of terminal olefins was not described there.

However, the terminally hydroformylated products are generally desired. Thus, for example, plasticizers (e.g. phthalates) obtained from alcohols produced by terminal hydroformylation of olefins and subsequent hydrogenation display more favourable properties when used in plastics (e.g. in PVC), for instance in respect of the elasticity, than do plasticizers based on branched aldehydes.

The hydroformylation of compounds having a plurality of double bonds usually also requires nonisomerizing, highly selective catalysts in order to obtain a discrete (individual) product.

Proceeding from the rhodium-bisphosphite catalysts described in EP 0 472 071, it was therefore an object of the present invention to provide alternative bisphosphite ligands which preferably favour terminal hydroformylation of terminal double bonds, (i.e. terminal hydroformylation leading to aldehydes having a high n/iso ratio) and particularly preferably have a low isomerization activity. The terminal double bonds should preferably be hydroformylated with a very high n/iso ratio. Furthermore, the bisphosphite ligands according to the invention should preferably have a higher hydrolysis stability than those described in EP 0 472 071.

It has surprisingly been found that this object is achieved by bisphosphite ligands of the formula I

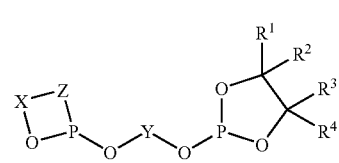

where

X=a divalent substituted or unsubstituted bisalkylene or bisarylene radical which may contain one or more heteroatom(s), Y=a divalent substituted or unsubstituted bisarylene or bisalkylene radical which may contain one or more heteroatom(s), Z=oxygen or $NR^9$, $R^1R^2$, $R^3$, $R^4$ are identical or different, substituted or unsubstituted, linked, unlinked, fused or unfused aryl or heteroaryl radicals and R⁹=hydrogen or a substituted or unsubstituted alkyl or aryl radical which may contain one or more heteroatom(s).

The present invention accordingly provides bisphosphites of the formula I

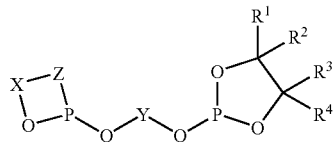

I where

X=a divalent substituted or unsubstituted bisalkylene or bisarylene radical which may also contain heteroatoms, Y=a divalent substituted or unsubstituted bisarylene or bisalkylene radical, Z oxygen or NR⁹, $R^1$, $R^2$, $R^3$, $R^4$ are identical or different, substituted or unsubstituted, linked, unlinked, fused or unfused aryl or heteroaryl radicals and $R^9$=hydrogen or a substituted or unsubstituted alkyl or aryl radical, and also metal complexes which have such a bisphosphite of the formula I as ligand.

The present invention likewise provides a process for preparing the bisphosphites of the formula I.

In addition, the present invention provides for the use of a bisphosphite of the formula I or a metal complex containing a bisphosphite of the formula I in catalytic reactions, in particular in hydroformylation.

The compounds according to the invention have the following advantages: compared to the ligands described in EP 0 472 071, the bisphosphites of the invention display a low isomerization activity when used as ligands in hydroformylation. In addition, terminal double bonds are hydroformylated highly selectively while internal double bonds remain virtually unaffected when catalysts produced from the ligands according to the invention are used. Thus, for example, the terminal double bonds can be hydroformylated with high selectivity in the hydroformylation of olefins which have both internal and terminal double bonds. Alternatively, the constituents which bear terminal double bonds can be hydroformylated selectively in an olefin mixture. The terminal double bonds are terminally hydroformylated highly selectively, i.e. with a high n/iso ratio. Furthermore, the ligands according to the invention display a high stability, in particular towards aqueous hydrolysis.

The bisphosphites of the invention and a process for preparing them and also their use are described by way of example below, without the invention being restricted to these illustrative embodiments. If ranges, general formulae or classes of compounds are referred to below, these are intended to encompass not only the corresponding ranges or groups of compounds which are explicitly mentioned but also all subranges and subgroups of compounds which can be obtained by taking out individual values (ranges) or compounds. If documents are cited in the present description, their contents are fully incorporated by reference into the disclosure content of the present text.

The bisphosphite of the invention has the formula I,

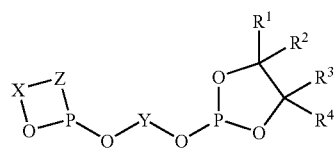

I where

X=a divalent substituted or unsubstituted bisalkylene or bisarylene radical which may contain one or more heteroatom(s), Y=a divalent substituted or unsubstituted bisarylene or bisalkylene radical which may contain one or more heteroatom(s), Z=oxygen or NR⁹, $R^1R^2$, $R^3$, $R^4$ are identical or different, substituted or unsubstituted, linked, unlinked, fused or unfused aryl or heteroaryl radicals and R⁹=hydrogen or a substituted or unsubstituted alkyl or aryl radical which may contain one or more heteroatom(s). The radicals $R^1$, $R^2$, $R^3$, $R^4$, $R^9$, X or Y may, for example, be substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, —$CF_3$, —$(CH_2)_i(CF_2)_jCF_3$ where i=0-9 and j=0-9, —$SiR^{21}_3$, —$Si(OR^{21})_3$, —$SiR^{21}(OR^{21})_2$, —$SiR^{21}_2OR^{21}$, —$OSiR^{21}_3$, —$OSi(OR^{21})_3$, —$OSiR^{21}(OR^{21})_2$, —$OSiR^{21}_2OR^{21}$, —$OR^{21}COR^{19}$, —$CO_2R^{19}$, —$CO_2M$, —$SO_2R^{19}$, —$SOR^{19}$, —$SO_3R^{19}$, —$SO_3M$, —$SO_2NR^{19}R^{20}$, —$NR^{19}R^{20}$ or —$N=CR^{19}R^{20}$, where $R^{19}$, $R^{20}$ and $R^{21}$ are selected independently from among H, monovalent substituted or unsubstituted aliphatic and aromatic hydrocarbon radicals having from 1 to 25 carbon atoms but $R^{21}$=H is excluded and M is an alkali metal ion, formally half an alkaline earth metal ion, an ammonium ion or a phosphonium ion. Preferred substituents, in particular for the radicals X and Y, are tert-butyl and methoxy groups. The radicals $R^1$, $R^2$, $R^3$, $R^4$ are preferably unsubstituted phenyl radicals. Such radicals can, for example, be radicals as are present in the formulae I-1, I-2 or I-3,

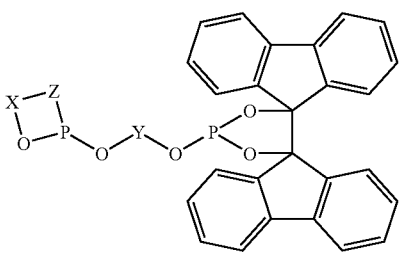

I-1

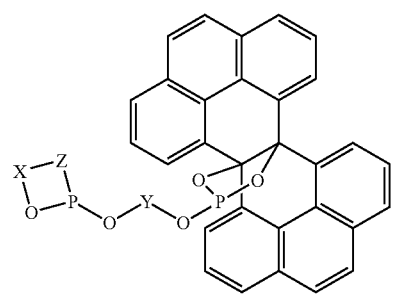

I-2

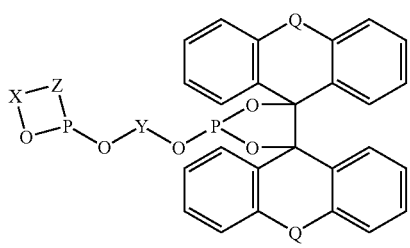

I-3 where the radicals Q can be, for example, identical or different and each be $CH_2$, $CR^9R^{10}$, $CHR^9$, O, NH or $NR^9$, where $R^9$ and $R^{10}$ can be identical or different and have the meanings given above for $R^9$.

In the bisphosphite of the invention, the radical X can be, in particular, a radical Xa,

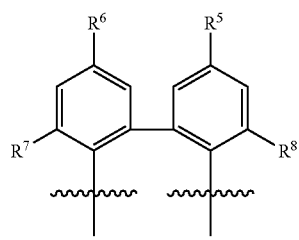

Xa

The radicals $R^5$, $R^6$, $R^7$, $R^8$ can be, independently of one another, substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms or H, F, Cl, Br, I, $-CF_3$, $-(CH_2)_i(CF_2)_jCF_3$ where i=0-9 and j=0-9, $-SiR^{21}_3$, $-Si(OR^{21})_3$, $-SiR^{21}(OR^{21})_2$, $-SiR_2OR^{21}$, $-OSiR^3$, $-OSi(OR^{21})_3$, $-OSiR^{21}(OR^{21})_2$, $-OSiR^{21}_2OR^{21}$, $-OR^{19}$, $COR^{19}$, $-CO_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$ or $-N=CR^{19}R^{20}$, where, $R^{19}$, $R^{20}$ and $R^{21}$ are selected independently from among H, monovalent substituted or unsubstituted aliphatic and aromatic hydrocarbon radicals having from 1 to 25 carbon atoms but $R^{21}$=H is excluded and M is an alkali metal ion, formally half an alkaline earth metal ion, an ammonium ion or a phosphonium ion. The radicals $R^5$, $R^6$, $R^7$, $R^8$ may, for example, be substituted by one or more radicals selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, $-CF_3$, $-(CH_2)_i(CF_2)_jCF_3$ where i=0-9 and i=0-9, $-SiR^{21}_3$, $-Si(OR^{21})$, $-SiR^{21}(OR^{21})_2$, $-SiR^{21}_2OR^{21}$, $-OSiR^{21}_3$, $-OSi(OR^{21})_3$, $-OSiR^{21}(OR^{21})_2$, $-OSiR^{21}_2OR^2$, $-OR^{19}$, $-COR^{19}$, $-CO_2R^{19}$, $-CO_2M$, $-SO_2R^{19}$, $-SOR^{19}$, $-SO_2R^{19}$, $-SO_3M$, $-SO_2NR^{19}R^{20}$, $-NR^{19}R^{20}$ or $-N=CR^{19}R^{20}$, where $R^{19}$, $R^{20}$, $R^{21}$ and M can have the above meanings. In the case of the radical Xa, the radicals $R^5$ to $R^8$ are preferably hydrogen, alkoxy groups, in particular methoxy groups or tert-butyl groups. The radicals $R^5$ and $R^6$ and the radicals $R^7$ and $R^8$ are preferably identical pairwise in each case. Particular preference is given to the radicals $R^5$ and $R^6$ being methoxy groups and/or the radicals $R^7$ and $R^8$ being tert-butyl groups.

In the bisphosphite of the invention, X is preferably an ethylene radical substituted by radicals $R^{1'}$, $R^{2'}$, $R^{3'}$ and $R^{4'}$, where the radicals $R^{1'}$, $R^{2'}$, $R^{3'}$ and $R^{4'}$ can be identical or different, substituted or unsubstituted, linked, unlinked or fused aryl or heteroaryl radicals. Possible substituents for the radicals $R^{1'}$ to $R^{4'}$ are the substituents mentioned for the radicals $R^1$ to $R^4$. Particularly preferred bisphosphites are symmetrical bisphosphites, i.e. ones in which X is an ethylene radical substituted by the radicals $R^{1'}$, $R^{2'}$, $R^{3'}$ and $R^{4'}$ with the radicals $R^1$ and $R^{1'}$, $R^2$ and $R^{2'}$, $R^3$ and $R^{3'}$ and $R^4$ and $R^{4'}$ in each case being identical.

The divalent radical Y in the bisphosphite of the invention can preferably be a substituted or unsubstituted bisphenyl radical or bisnaphthyl radical. Possible substituents can be the abovementioned substituents. The radical Y is preferably selected from among the bisphenoxy radicals of the formulae IIa to IId

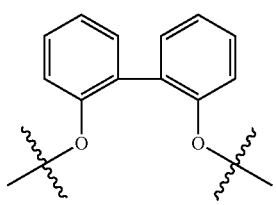

IIa

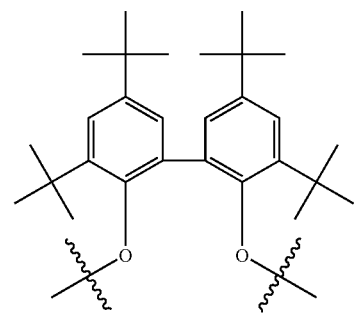

IIb

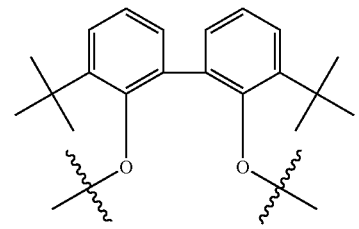

IIc

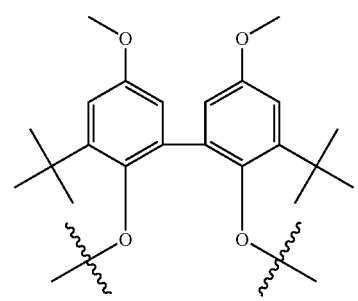

IId or bisnaphthoxy radicals of the formula III

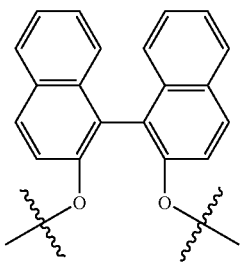

III which can be present in racemic, atropisomerically enriched or atropisomerically pure form.

Particularly preferred bisphosphites according to the invention are the bisphosphites of the formulae Ia to Ic below, with Ic being able to be prepared and used as racemate or in atropisomerically enriched or atropisomerically pure form.

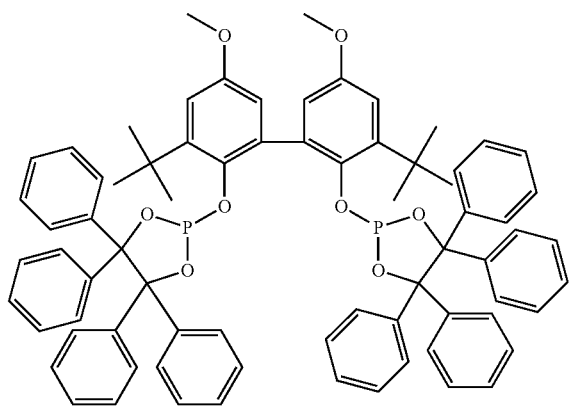

Ia

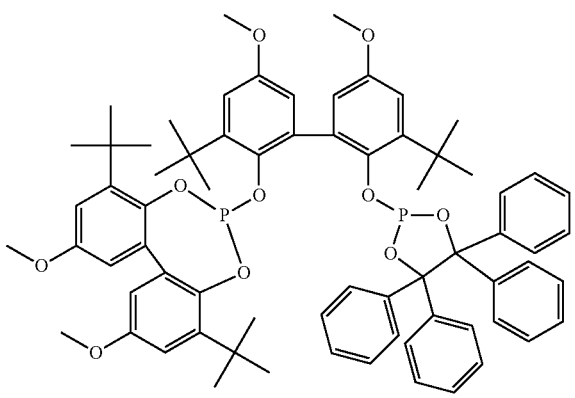

Ib

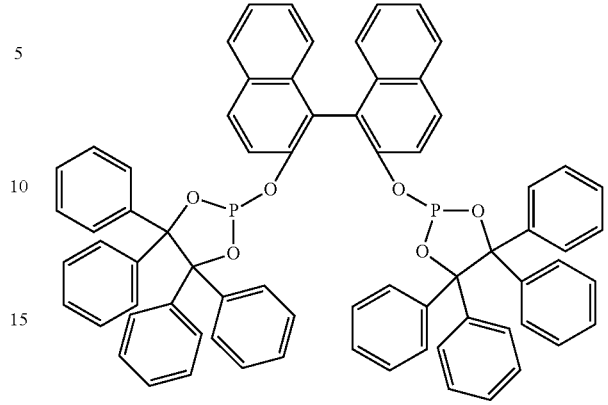

Ic

The bisphosphites of the invention display a high hydrolysis stability and are therefore particularly suitable for use as ligands. The use of enantiomerically pure bisphosphites enables the hydroformylation to be carried out as an asymmetric hydroformylation.

The bisphosphites of the invention are suitable ligands for complexing metals of Group 4, 5, 6, 7, 8, 9 or 10 of the Periodic Table of the Elements. A phosphite-metal complex according to the invention is therefore characterized in that it contains a metal of Group 4, 5, 6, 7, 8, 9 or 10 of the Periodic Table of the Elements and one or more bisphosphites according to the invention. The complexes can contain one or more phosphite ligands and, if desired, further ligands. Examples of suitable metals are rhodium, cobalt, iridium, nickel, palladium, platinum, iron, ruthenium, osmium, chromium, molybdenum and tungsten. The metal in the phosphite-metal complex of the invention is preferably rhodium, palladium, nickel, platinum, cobalt or ruthenium.

The bisphosphites of the invention or the metal complexes of the invention can be used in catalysis, in particular in homogeneous catalysis. Particularly when using metals of Group 8, 9 or 10, the resulting metal complexes can be used as catalysts for hydro-formylation, carbonylation, hydrogenation and hydro-cyanation reactions; particular preference is given to rhodium, cobalt, nickel, palladium, platinum and ruthenium.

It can be particularly advantageous for the bisphosphites of the invention or the metal complexes of the invention to be used in the catalytic hydroformylation of olefins, preferably of olefins having from 2 to 50 carbon atoms, preferably from 3 to 25, particularly preferably from 6 to 12 and very particularly preferably 8, 9, 10, 11 or 12, carbon atoms. Preference is given to using a metal complex having rhodium or cobalt as metal in the hydroformylation. The molar ratio of metal, preferably a metal of Group 8, to bisphosphite in the reaction mixture of the hydroformylation is preferably from 1:1 to 1:500, more preferably from 1:1 to 1:200 and particularly preferably from 1:2 to 1:50. The presence of the bisphosphite of the invention as free ligand in the reaction mixture can be achieved by means of a molar ratio of metal to bisphosphite of 1:>1, particularly preferably 1:>2.

When rhodium is used as catalyst metal, particularly high catalytic activities can be obtained in hydroformylation reactions. Catalysts which contain rhodium and bisphosphite according to the invention display an astonishingly low isomerization activity and a high preference for terminal double bonds and a high proportion of linear products and are therefore particularly suitable for the selective terminal hydroformylation of terminal olefins. They can also be used to hydroformylate the terminal olefins selectively in olefin mixtures or compounds having terminal and internal double bonds, with the internal double bonds remaining largely unaffected.

The catalyst metals can be used in the form of salts or complexes, in the case of rhodium as, for example, rhodium carbonyls, rhodium nitrate, rhodium chloride, $Rh(CO)_2$ (acac) (acac=acetylacetonate), rhodium acetate or rhodium carboxylates, for example rhodium octanoate.

The active catalyst species for homogeneous catalysis is formed from the bisphosphite ligands according to the invention and the catalyst metal under reaction conditions. During the hydroformylation, contact of the bisphosphite ligand of the invention and the catalyst metal with synthesis gas presumably forms a carbonyl hydrido phosphite complex as active catalyst species. The bisphosphites and, if desired, further ligands can be added in free form together with the catalyst metal (as salt or complex) to the reaction mixture in order to generate the active catalyst species in situ. It is also possible to use a phosphite-metal complex according to the invention which contains the abovementioned bisphosphite ligands and the catalyst metal as precursor for the actual catalytic active complexes. These phosphite-metal complexes are prepared by reacting the corresponding catalyst metal of Groups 4 to 10 in the form of a chemical compound or in the oxidation state 0 with the bisphosphite ligand of the invention.

Fresh bisphosphite according to the invention can be added to the reaction at any point in time, for example to keep the concentration of free ligand constant.

The concentration of the metal in the reaction mixture, in particular in the hydroformylation mixture, is preferably from 1 ppm by mass to 1000 ppm by mass and more preferably from 5 ppm by mass to 300 ppm by mass, based on the total weight of the reaction mixture.

The hydroformylation reactions carried out using the bisphosphites of the invention or the corresponding metal complexes can be carried out according to known methods, as described, for example, in J. FALBE, "New Syntheses with Carbon Monoxide", Springer Verlag, Berlin, Heidelberg, N.Y., page 95 ff., (1980). The olefin compounds are here reacted with a mixture of CO and $H_2$ (synthesis gas) in the presence of the catalyst to form the aldehydes having one more carbon atom.

The reaction temperatures for a hydroformylation process in which the bisphosphites or phosphite-metal complexes of the invention can be used are preferably from 40° to 180° C., more preferably from 75° C. to 140° C. and particularly preferably from 90 to 120° C. The pressure under which the hydroformylation is carried out is preferably from 1 to 300 bar and more preferably from 10 to 64 bar of synthesis gas. The molar ratio of hydrogen to carbon monoxide ($H_2$/CO) in the synthesis gas is preferably from 10/1 to 1/10 and particularly preferably from 1/1 to 2/1.

The catalyst or the ligand/the bisphosphite of the invention is preferably homogeneously dissolved in the hydroformylation mixture comprising starting materials (olefins and synthesis gas) and products (aldehydes, alcohols, by-products formed in the process, in particular high boilers). If desired, solvents or solvent mixtures and/or stabilizer compounds or promoters can additionally be used.

Owing to their relatively high molecular weight, the bisphosphites of the invention have a low volatility. They can therefore easily be separated off from the more volatile reaction products. They are sufficiently soluble in customary organic solvents.

The starting materials for the hydroformylation can be organic compounds, in particular olefins or mixtures of olefins, preferably olefins having from 2 to 50, more preferably from 3 to 25, carbon atoms, in particular olefins having one or more terminal or internal C=C double bonds. They can have a linear, branched or cyclic structure. Examples are propene, 1-butene, cis-2-butene, trans-2-butene, isobutene, butadiene, mixtures of $C_4$-olefins; $C_5$-olefins such as 1-pentene, 2-pentene, 2-methyl-1-butene, 2-methyl-2-butene, 3-methyl-1-butene, $C_6$-olefins such as 1-hexene, 2-hexene, 3-hexene, the $C_6$-olefin mixture obtained in the dimerization of propene (dipropene); $C_7$-olefins such as 1-heptene, further n-heptenes, 2-methyl-1-hexene, 3-methyl-1-hexene; $C_8$-olefins such as 1-octene, further n-octenes, 2-methylheptenes, 3-methylheptenes, 5-methyl-2-heptene, 6-methyl-2-heptene, 2-ethyl-1-hexene, the isomeric $C_8$-olefin mixture obtained in the dimerization of butenes (dibutene), $C_9$-olefins such as 1-nonene, further n-nonenes, 2-methyloctenes, 3-methyloctenes, the $C_9$-olefin mixture obtained in the trimerization of propene (tripropene), $C_{1-10}$-olefins such as n-decenes, 2-ethyl-1-octene; $C_{12}$-olefins such as n-dodecenes, the $C_{12}$-olefin mixture obtained in the tetramerization of propene or the trimerization of butenes (tetrapropene or tributene), $C_{14}$-olefins such as n-tetradecenes, $C_{16}$-olefins such as n-hexadecenes, the $C_{16}$-olefin mixture obtained in the tetramerization of butenes (tetrabutene) and also olefin mixtures prepared by cooligomerization of olefins having different numbers of carbon atoms (preferably from 2 to 4), if desired after separation into fractions having an identical or similar number of carbon atoms by distillation. It is likewise possible to use olefins or olefin mixtures produced by Fischer-Tropsch synthesis and also olefins or organic compounds having C—C double bonds which are obtained by oligomerization of ethene or are obtainable via metathesis reactions or telomerization reactions, e.g. methyl octa-2,7-dienyl ether.

Preferred starting materials are in general α-olefins such as propene, 1-butene, 1-hexene or 1-octene, dimers or trimers of butene (dibutene, di-n-butene, diisobutene, tributene) and also methyl octa-2,7-dienyl ether.

It can be advantageous for compounds having stabilizing properties, in particular stabilizing properties in respect of the stability of the ligands or the catalyst complex to be present in the hydroformylation reaction mixture. Such compounds which can be used as stabilizers are, for example, sterically hindered amines as are described, for example, in WO 2005/039762, in particular sterically hindered secondary amines as are described, for example, in DE 10 2005 042 464.

The hydroformylation can be carried out continuously or batchwise. Examples of industrial embodiments are stirred vessels, bubble columns, jet nozzle reactors, tube reactors or loop reactors, some of which can be cascaded and/or provided with internals.

The reaction can be carried out as a single stage or in one or more stages. The separation of the aldehyde compounds formed and the catalyst can be carried out by a conventional method. This can be effected industrially by means of, for example, a distillation, a falling film evaporator or a thin film evaporator. This applies particularly when the catalyst is separated off as a solution in a high-boiling solvent from the lower-boiling products. The catalyst solution which has been separated off can be used for further hydroformylations. When lower olefins (e.g. propene, butene, pentene) are used, discharge of the products from the reactor via the gas phase is also possible.

The bisphosphites of the invention can be prepared by a sequence of reactions of phosphorus halides with alcohols, in which halogen atoms on the phosphorus are replaced by oxygen groups. A suitable synthesis route is described below.

Thus, the bisphosphite of the invention can, for example, be obtained by means of a process which comprises the following steps
1) reaction of a diol Aa or an alcohol amine Ab with phosphorus trihalide to form an intermediate A,
2) reaction of a tetraarylethanediol Ca, which can bear identical or different, substituted or unsubstituted, linked or unlinked, fused or unfused aryl or heteroaryl radicals, with phosphorus trihalide to form an intermediate C,
3) reaction of the intermediate A or C with a diol Ba to form an intermediate B and
4) reaction of the intermediate B with the intermediate A or C which was not used in process step 3).

The reaction of the diols with the phosphorus trihalide can be carried out directly or can comprise an intermediate step. It can be advantageous for the diols Aa, Ba, Ca, and the alcohol amine Ab and/or the intermediate C to be reacted in steps 1), 2), 3) and/or 4) with a metal compound to form the corresponding metal salt which is then reacted with the phosphorus trihalide. In this way, no hydrohalide impurities, in particular amine hydrochloride impurities which are relatively difficult to separate off, are formed in the reaction but instead salts which are relatively sparingly soluble in the reaction medium and can thus be separated off easily, e.g. by filtration, are formed. In addition, this intermediate step makes the use of nucleophilic bases possible. As metal compound, it is possible to use, for example, sodium hydride, methyllithium or butyllithium. As phosphorus trihalide, it is possible to use, for example, $PCl_3$, $PBr_3$ and $PI_3$. Preference is given to using phosphorus trichloride ($PCl_3$) as phosphorus trihalide.

It can be advantageous to carry out the reaction with phosphorus trihalide in the presence of a base. The use of a suitable base enables the hydrogen halide formed in the reaction of the phosphorus halides to be scavenged or catalysed. A tertiary amine is preferably used as base. Tertiary amines which can be used are, for example, triethylamine, pyridine or N-butyl-dimethylamine. To scavenge the hydrogen halide formed, preference is given to using at least such an amount of base that the hydrogen halide formed can be scavenged completely.

Since the diols used and their reaction products are frequently solid, the reactions are preferably carried out in a solvent. As solvents, it is possible to use, for example, aprotic solvents which react neither with the alcohols nor with the phosphorus compounds. Suitable solvents are, for example, ethers such as diethyl ether, tetrahydrofuran (THF) or MTBE (methyl tert-butyl ether) or aromatic hydrocarbons such as toluene.

The solvents used should preferably be very largely free of water and oxygen. Preference is given to using solvents having a water content of from 0 to 500 ppm by mass, particularly preferably from 5 to 250 ppm by mass. The water content can, for example, be determined by the Karl Fischer method.

If drying of the solvents used is necessary, it can be effected by distillation of the solvent over a suitable desiccant or by passing the solvent through a cartridge or column filled, for example, with molecular sieve 4 Å.

The process steps for preparing the bisphosphites in the process of the invention are preferably carried out at a temperature of from −80° C. to 150° C., preferably from −20° C. to 110° C. and particularly preferably from 0° C. to 80° C.

The four substeps of the process are shown by way of example below. In this embodiment of the process of the invention, a diol Aa is firstly reacted with phosphorus trichloride to form the intermediate A.

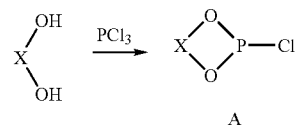

A tetraarylethanediol Ca, which can but does not have to be identical with the diol from the preceding step 1), is reacted with phosphorus trichloride to form the monohalophosphite C.

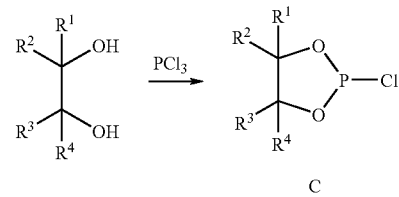

The intermediate A is reacted with a diol Ba to form the monophosphite B.

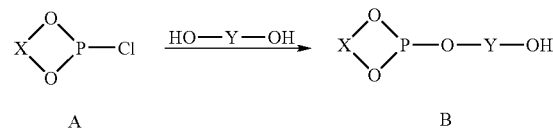

Intermediate B is subsequently reacted with intermediate C to form the desired bisphosphite D.

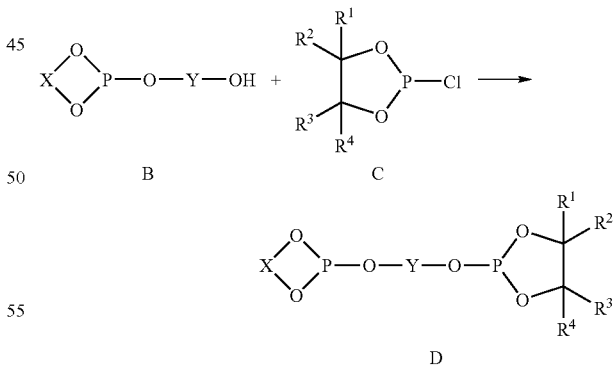

This synthetic route is only one of many and merely illustrates the basic procedure. It is also possible, for example, for C firstly to be reacted with HO—Y—OH (Ba) and A subsequently to be added. In the case of symmetrical bisphosphites, i.e. when $X=R^1R^2C-CR^3R^4$, the process steps 1) and 2) and also 3) and 4) can in each case be combined in one step.

As starting compound in the process of the invention, it is possible to use a diol Aa or an alcohol amine Ab.

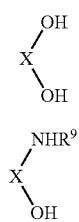

Aa

Ab

If the compound used is a diol Aa, the radical X is preferably a divalent substituted or unsubstituted bis-alkylene or bisarylene radical. Possible substituents on the bisalkylene or bisarylene radicals can be the substituents mentioned for formula I.

As diol Aa in the process of the invention, preference is given to using a compound in which the radical X is, in particular, a radical Xa.

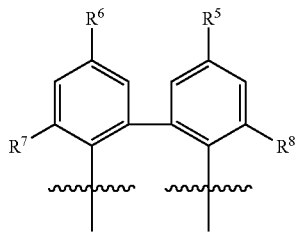

Xa

The radicals $R^5$, $R^6$, $R^7$, $R^8$ can be, independently of one another, substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms or H, F, Cl, Br, I, $-CF_3$, $-(CH_2)_i(CF_2)_jCF_3$ where i=0-9 and j=0-9, $-SiR^{21}_3$, $-Si(OR^{21})_3$, $-SiR^{21}(OR^{21})_2$, $-SiR^{21}_2OR^{21}OR^{21}$, $-OSiR^{21}_3$, $-OSi(OR^{21})_3$, $-OSiR^{21}(OR^{21})_2$, $-OSiR^{21}_2OR^{19}OR^{21}COR^{19}$, $C_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$ or $-N=CR^{19}R^{20}$, where $R^{19}$, $R^{20}$ and $R^{21}$ are selected independently from among H, monovalent substituted or unsubstituted aliphatic and aromatic hydrocarbon radicals having from 1 to 25 carbon atoms but $R^{21}=H$ is excluded and M is an alkali metal ion, formally half an alkaline earth metal ion, an ammonium ion or a phosphonium ion. The radicals $R^5$, $R^6$, $R^7$, $R^8$ may, for example, be substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, $-CF_3$, $-(CH_2)_i(CF_2)_jCF_3$ where i=0-9 and j=0-9, $-SiR^{21}_3$, $-Si(OR^{21})_3$, $-SiR^{21}(OR^{21})_2$, $-SiR^{21}_2OR^{21}$, $-OSiR^{21}_3$, $-OSi(OR^{21})_3$, $-OSiR^{21}(OR^{21})_2$, $-SiR^{21}_2OR^{21}$, $-OSiR^{21}_3$, $-OSi(OR^{21})_3$, $-OSiR^{21}(OR^{21})_2$, $-OSiR^{21}_2OR^{21}$, $-OR^{19}$, $-COR^{19}$, $-CO_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$ or $-N=CR^{19}R^{20}$, where $R^{19}$, $R^{20}$, $R^{21}$ and M can have the above meanings. In the case of the radical Xa, the radicals $R^5$ to $R^8$ are preferably hydrogen, alkoxy groups, in particular methoxy groups or tert-butyl groups. The radicals $R^5$ and $R^6$ and the radicals $R^7$ and $R^8$ are preferably identical pairwise in each case. Particular preference is given to the radicals $R^5$ and $R^6$ being methoxy groups and/or the radicals $R^7$ and $R^8$ being tert-butyl groups.

It can be advantageous to use a diol Aa in which X is preferably an ethylene radical substituted by radicals $R^{1'}$, $R^{2'}$, $R^{3'}$ and $R^{4'}$ where the radicals $R^{1'}$, $R^{2'}$, $R^{3'}$ and $R^{4'}$ can be identical or different, substituted or unsubstituted, aryl radicals. Possible substituents for the radicals $R^{1'}$ to $R^{4'}$ are the substituents mentioned for the radicals $R^1$ to $R^4$. If a diol Ca having the radicals $R^1$ to $R^4$ and a diol Aa in which X is an ethylene radical substituted by the radicals $R^1$, $R^2$, $R^{3'}$ and $R^{4'}$ are used and the radicals $R^1$ and $R^{1'}$, $R^{2'}$ and $R^{2'}$, $R^3$ and $R^{3'}$ and $R^4$ and $R^{4'}$ are in each case identical, a symmetrical bisphosphite according to the invention, e.g. a compound of the formula Ia or Ic, can be prepared. As indicated above, the process steps 1) and 2) or 3) and 4) can in each case be combined or carried out together when the starting compounds Aa and Ca are identical.

As diol HO—Y—OH (Ba), it is possible to use, in particular, diols in which the divalent radical Y is a substituted or unsubstituted bisarylene or bisalkylene radical, preferably a bisphenoxy or bisnaphthoxy radical. Possible substituents can be the substituents mentioned for formula I. Preference is given to using a diol Ba whose radical Y is selected from among the bisphenyl radicals of the formulae IIa to IId

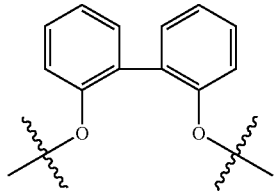

IIa

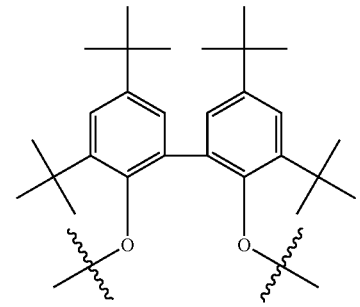

IIb

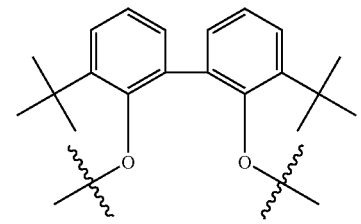

IIc

-continued

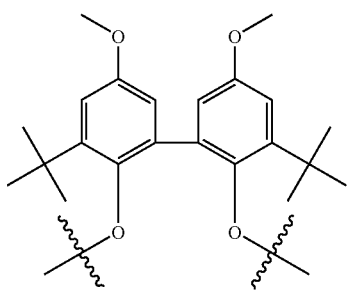

IId or bisnaphthyl radicals of the formula III in racemic, enantiomerically enriched or enantiomerically pure form

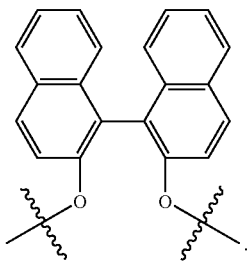

III

As tetraarylethanediol Ca,

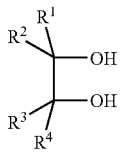

Ca it is possible to use tetraarylethanediols which have substituted or unsubstituted, linked, unlinked or fused aryl or heteroaryl radicals $R^1$ to $R^4$. The radicals $R^1$ to $R^4$ can be identical or different. Possible aryl radicals are, for example, phenyl radicals, naphthyl radicals. The radicals $R^1$ to $R^4$ can also be linked or fused with one another, e.g. 9-fluorenyl radicals, phenanthryl radicals, xanthenyl radicals and heteroaromatics.

Preference is given to using benzopinacol or benzo-pinacol substituted on the phenyl radicals as tetra-arylethanediol Ca. Possible substituents on the radicals $R^1$ to $R^4$ or the benzopinacol are the substituents mentioned for formula I.

The following examples illustrate the process of the invention without restricting its scope, which is defined by the description and the claims.

EXAMPLES

All preparations were carried out by means of standard Schlenk vessel techniques using argon (argon 5.0, Linde AG) as protective gas. Tetrahydrofuran and toluene were dried over potassium (THF) or sodium (toluene) before use. NMR spectra were recorded using a Bruker ARX 400, and elemental analyses were carried out using a LECO CHNS 932.

Example 1

Synthesis of 1-chloro-3,3,4,4-tetraphenyl-phospholane (C-1)

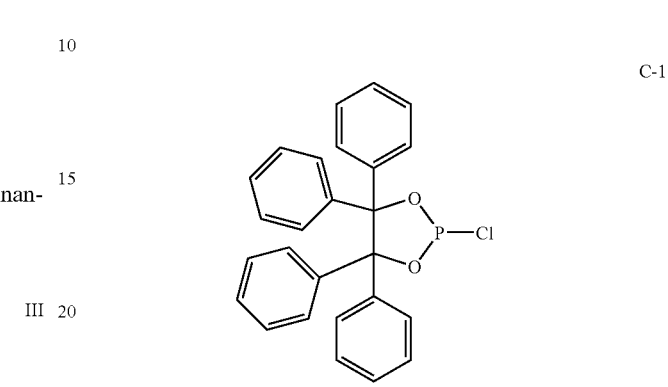

C-1

A 0.768 molar solution of phosphorus trichloride (Aldrich, 99%) in tetrahydrofuran (10.7 ml; 8.22 mmol) was added dropwise to a suspension of 1.878 g (5.12 mmol) of benzopinacol (Acros, 98%) in 30 ml of tetrahydrofuran (Sigma-Aldrich, 99.9%) at −40° C. while stirring and a solution of 1.56 g (15.4 mmol) of triethylamine (Aldrich, AR) in 4 ml of tetrahydrofuran was subsequently added dropwise, resulting in formation of a voluminous colourless precipitate. The mixture was allowed to warm to room temperature and was stirred for a further 5 hours. The reaction mixture was filtered through a G4 frit and the filtrate was dried at 40° C. at 20 mbar for 1.5 hours. The viscous residue was taken up in toluene (15 ml). This solution was filtered through a G4 frit, the filtrate was evaporated at 20 mbar and subsequently dried at a bath temperature of 40° C. and $10^{-1}$ mbar for 2 hours. This gave 2.32 g (90% of theory, calculated as toluene adduct) of a highly viscous liquid which still contains 0.8 equivalents of toluene. Analysis: $^{31}P\{1H\}$-NMR($C_6D_6$) $\delta$=173.44 ppm.

Synthesis of D-1

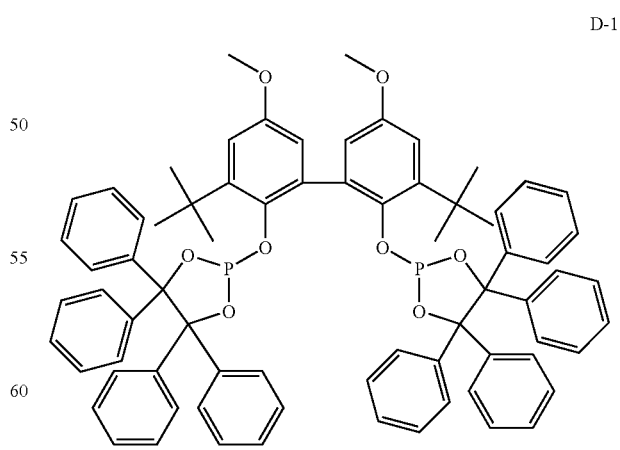

D-1

4 mmol of a solution of n-butyllithium (Aldrich) in 8 ml of hexane (Riedel-de-Haën, 97%) were added dropwise to 0.717 g (2 mmol) of the compound 2,2'-bis(6-tert-butyl-1-hydroxy-4-methoxyphenyl) (prepared by the method described by F.

R. Hewgill and D. G. Hewitt in Journal of the Chemical Society C, 1967, 8, 726-730) in tetrahydrofuran (Riedel-de-Haën, Chromasolv) (8 ml) at −20° C. while stirring. The mixture was stirred at −20° C. for 20 minutes, subsequently warmed to room temperature and a solution of 1.90 g (4.4 mmol) of C-1 in tetrahydrofuran (16 ml) was then added dropwise. After stirring overnight at 25° C., the solvent was removed at $10^{-1}$ mbar. The product obtained was stirred with 40 ml of toluene (Riedel-de-Haën, 99.7%), filtered and the residue on the frit was washed with toluene. The filtrates obtained were concentrated at $10^{-1}$ mbar and the residue was dried at 40° C. for 2 hours. The solid obtained was taken up in 32 ml of acetonitrile (Riedel-de-Haën, 99.9%) and heated briefly until a clear solution was present. On cooling, D-1 precipitated. It was filtered off and the remaining solvent was taken off at 40° C. and $10^{-1}$ mbar for 3 hours to give 1.9 g (82%) of the target substance.

$^{31}P\{^{1}H\}$-NMR ($C_6D_6$, 202 MHz): δ=145.62 ppm. $^{1}$H-NMR (500 MHz, $C_6D_6$): δ=1.39 (s, 18H), 3.32 (s, 6H), 6.84-6.88 (m, 7H), 6.89-6.94 (m, 7H), 6.95-7.00 (m, 4H), 7.04-7.09 (m, 8H), 7.21-7.30 (m, 10H), 7.57 (d, J=7.5 Hz, 4H), 7.65 (d, J=7.5 Hz, 4H) ppm. Elemental analysis (calc. for $C_{74}H_{68}O_8P_2$=1147.29 g/mol): C 77.00 (77.47); H 5.66 (5.97); P 5.82 (5.40) %.

Example 2

Synthesis of A-1

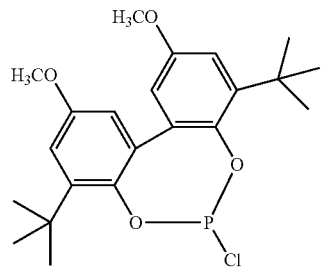

A-1

A1 was prepared from 2,2'-bis(6-tert-butyl-1-hydroxy-4-methoxyphenyl) (prepared by the method described by F. R. Hewgill and D. G. Hewitt in Journal of the Chemical Society C, 1967, 8, 726-730) by the method reported in EP 1 209 164.

Synthesis of B-2

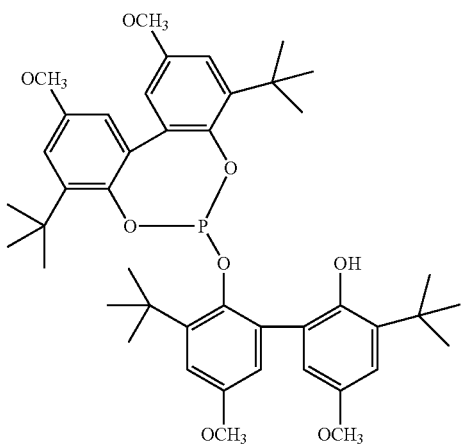

B-2

B-2 was prepared from A-1 by the method described in EP 1 209 164 (Example 2).

Synthesis of D-2

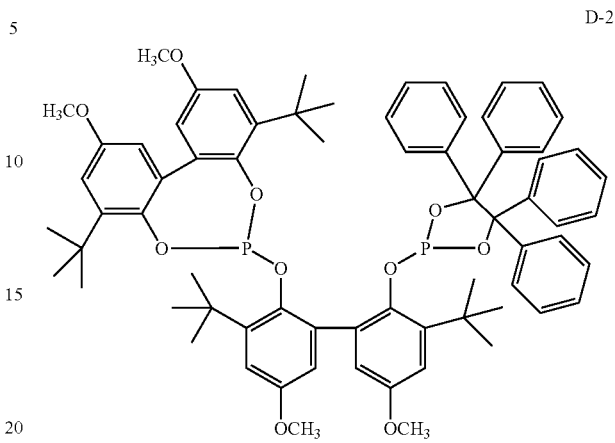

D-2 n-Butyllithium (2.014 mmol) in hexane (4 ml) was added dropwise while stirring to a solution of B-2 (1.5 g; 2.014 mmol) in THF (8 ml) which had been cooled to −20° C. 20 minutes after the addition was complete, the mixture was brought to room temperature and a solution of 2-chloro-4,4', 5,5'-tetraphenyl-1,3,2-dioxaphospholane (C-1) (0.868 g; 2.014 mmol) in THF (8 ml) was slowly added dropwise. The mixture was stirred at room temperature for 4 hours, the solvent was then removed at 40 mbar and the residue was dried at 40° C. and $10^{-1}$ mbar and subsequently stirred with toluene (30 ml). After filtration, the filtrate was evaporated and the white solid obtained was dried at $10^{-1}$ mbar (40° C., 2 h). The crude product was stirred with 40 ml of boiling acetonitrile. This mixture was stored in a refrigerator, then filtered and the filter cake was washed with ice-cold acetonitrile. Drying at $10^{-1}$ mbar gave 1.6 g (1.404 mmol=70% of theory) of product. Analysis (calc. for $C_{70}H_{76}O_{10}P_2$=1139.31 g/mol): C 73.61 (73.80); H 6.99 (6.72); P 5.46 (5.44) %. $^{31}$P-NMR ($CD_2Cl_2$) δ 135.4 (d, $J_{PP}$=38.9 Hz); 142.9 ppm (d, $J_{PP}$=38.9 Hz).

$^{1}$H-NMR ($CD_2Cl_2$) δ 1.26; 1.28; 1.38; 1.46 (4× s, each 9H); 3.48; 3.81; 3.82; 3.86 (4× s, each 3H); 6.42 (m, 1H); 6.69 (m, 1H); 6.78 (m, 1H); 6.94-7.10 (m, 18H); 7.19-7.25 (m, 5H); 7.61 (m, 2H) ppm.

Example 3

Synthesis of D-3

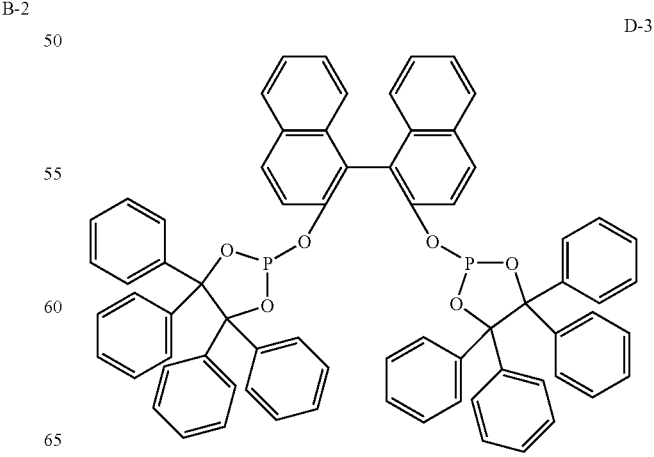

D-3

Triethylamine (0.992 g; 9.81 mmol) was firstly added at room temperature to a suspension of rac-1,1'-bi(2-naphthol) (0.891 g, 3.113 mmol, Aldrich, 99%) in 18 ml of toluene and a solution of C-1 (2.951 g; 6.85 mmol) in 26 ml of toluene was then added at 0° C. while stirring. The mixture was stirred at 0° C. for another 45 minutes and then at 80° C. for 16 hours. The product obtained was filtered, the solvent was removed at 20 mbar and the residue was stirred with 10 ml of toluene and filtered again. The filtrate was evaporated, the highly viscous residue obtained was dried at 55° C. and $10^{-1}$ mbar for 2 hours and subsequently recrystallized from acetonitrile. Yield: 2.684 g (2.496 mmol; 80% of theory). Analysis (calc. for $C_{72}H_{52}O_6P_2$=1075.14 g/mol) C 79.63 (80.43); H 4.69 (4.87); P 6.03 (5.76) %. $^{31}$P-NMR (CD$_2$Cl$_2$) δ 140.5 ppm.

Example 4

Comparative Hydroformylation Experiments using Ligands D-1, D-2, D-3 and Comparative Ligand D-4

The bisphosphite D-4 described in EP 0 472 071 was selected as comparative ligand. The synthesis of D-4 was carried out by a method analogous to that of EP 0 472 071. All examples using the known ligand D-4 serve merely for comparison and are therefore not according to the invention.

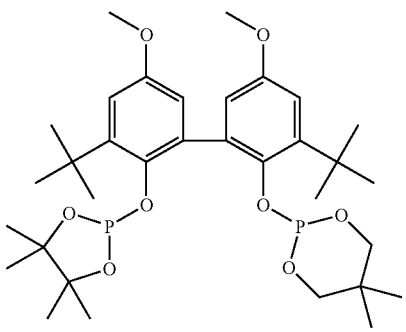

D-4

The hydroformylation was carried out in a 200 ml autoclave from Premex Reactor AG, Lengau, Switzerland, equipped with a pressure regulator to maintain a constant pressure, gas flow measurement, sparging stirrer and pressure pipette. To carry out the experiments, the following solutions of rhodium in the form of [(acac)Rh(COD)] (acac=acetylacetonate anion; COD=1.5-cyclooctadiene) (OMG AG & Co. KG, Hanau, Del.) as catalyst precursor in toluene were placed under an argon atmosphere in the autoclave: for experiments using 38.4 ppm by mass of rhodium: 10 ml of a 1.724 millimolar solution; for experiments using 96 ppm by mass of rhodium: 10 ml of a 4.31 millimolar solution. The appropriate amount of the phosphite compound dissolved in toluene, generally 5 equivalents of ligand per equivalent of rhodium, was subsequently added. The initial volume of the catalyst solution was adjusted to 41 ml by addition of further toluene. 15 ml of the olefin or olefin mixture indicated in each case in Table 1, whose mass had been determined beforehand, were placed in the pressure pipette. After replacement of the argon atmosphere by flushing with synthesis gas (Linde, H$_2$ (99.999%):CO (99.997%)=1:1), the autoclave was heated while stirring (1500 rpm) to the temperatures indicated in each case at a synthesis gas pressure of a) 33 bar for a final pressure of 50 bar, b) 12 bar for a final pressure of 20 bar and c) 7 bar for a final pressure of 10 bar. After the reaction temperature had been reached, the synthesis gas pressure was increased to a) 48 bar for a final pressure of 50 bar, b) 19 bar for a final pressure of 20 bar and c) 9.5 bar for a final pressure of 10 bar and the olefin (mixture) indicated in each case in Table 1 was injected by means of an overpressure of about 3 bar set in the pressure pipette. The reaction was carried out at a constant pressure of 50 or 20 or 10 bar (pressure regulator from Bronkhorst, NL) for a reaction time of 4 hours in each case. After the reaction time had elapsed, the autoclave was cooled to room temperature, vented while stirring and flushed with argon. 1 ml in each case of the reaction mixtures was taken off immediately after the stirrer had been switched off, diluted with 5 ml of pentane and analysed by gas chromatography.

GC-DATEN: HP 5890 Series II plus, PONA, 50 m×0.2 mm×0.5 μm; quantitative determination of residual olefin and aldehyde using the solvent toluene as internal standard.

Table 1 gives the results of the rhodium-catalysed hydroformylation of 1-octene (Aldrich, 98%), 2-pentene, propene (ABCR, cis+trans, 99%) and an isomer mixture of octenes which has a composition as described in DE 100 53 272, Examples 9 to 19.

In addition, Table 1 shows the results reported in EP 0 472 071 for the hydroformylation of 2 butene. Low conversions in the case of the octene mixture or in the case of 2-pentene and 2-butene indicate low isomerization activity, while high conversions point to considerable undesirable isomerization activity. The selectivity indicates the proportion of terminally hydroformylated substrate.

TABLE 1

Hydroformylation of terminal and internal olefins, experimental results

| Ligand | Substrate | Rh [ppm] | Ligand/ rhodium | Temp. [° C.] | Solvent | Pressure [bar] | Conversion [%] | n-Selectivity [%] |
|---|---|---|---|---|---|---|---|---|
| D-1 | 1-Octene | 38.4 | 5 | 120 | Toluene | 50 | 86 | 99 |
| D-2 | 1-Octene | 38.4 | 5 | 100 | Toluene | 50 | 70 | 94 |
| D-3 | 1-Octene | 38.4 | 5 | 100 | Toluene | 50 | 89 | 83 |
| D-4 | 1-Octene | 40 | 5 | 100 | Toluene | 50 | 94 | 85 |
| D-1 | n-Octenes | 96 | 5 | 120 | Toluene | 20 | 8 | 99 |
| D-2 | n-Octenes | 96 | 5 | 120 | Toluene | 20 | 19 | 77 |
| D-3 | n-Octenes | 96 | 10 | 120 | Toluene | 10 | 7 | 89 |
| D-4 | n-Octenes | 96 | 5 | 120 | Toluene | 20 | 54 | 33 |
| D-1 | 2-Pentene | 96 | 5 | 120 | Toluene | 20 | 14 | 99 |
| D-1 | 2-Pentene | 96 | 2 | 120 | Toluene | 20 | 14 | 99 |
| D-4 | 2-Pentene | 96 | 5 | 120 | Toluene | 20 | 86 | 60 |

TABLE 1-continued

Hydroformylation of terminal and internal olefins, experimental results

| Ligand | Substrate | Rh [ppm] | Ligand/ rhodium | Temp. [° C.] | Solvent | Pressure [bar] | Conversion [%] | n-Selectivity [%] |
|---|---|---|---|---|---|---|---|---|
| D-4 | 2-Pentene | 96 | 2 | 120 | Toluene | 20 | 80 | 60 |
| D-4[a] | 2-Butene | 90 | 4.8 | 90 | Texanol® | 25 | 52 | 31 |
| D-1[c] | Propene | 40 | 5 | 90 | Toluene | 20 | 84 | 97 |
| D-4[b] | Propene | 90 | 4.1 | 70 | Texanol® | 30 | 81 | 91 |

[a]taken from EP 0 472 071 (Example 9, Table 6, entry 3).
[b]taken from EP 0 472 071 (Example 3).
[c]in the presence of 0.0636 g of Tinuvin S (Ciba); conversion and selectivity after 5 h.

As can be seen from Table 1, all ligands displayed similar activities and selectivities in the hydroformylation of the terminal olefin, with D-1 achieving selectivities higher than any achieved hitherto. However, significant differences were apparent in the case of the octene mixture and in the case of the reaction of 2-pentene: while D1-D3 left the internal double bonds largely unaffected, the comparative substance D-4 displayed significant isomerization activity, as evidenced by high conversions (86% in the case of 2-pentene). In addition, the low selectivities in the case of D-4 indicate that a high proportion of branched aldehydes was formed. On the other hand, when D-1 was used, the small amounts (14%) of 2-pentene isomerized to 1-pentene were hydroformylated with a linearity of 99%. In addition, comparison with propene as substrate demonstrates the superior n/iso-selectivity of the ligand or catalyst complex of the invention.

Example 5

Hydroformylation of Methyl octa-2,7-dienyl Ether (MODE)

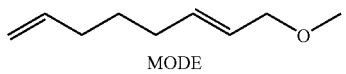

MODE

Methyl octa-2,7-dienyl ether (MODE) is a compound having a terminal double bond and an internal double bond. In this example, the terminal double bond is to be selectively hydroformylated while the internal double bond should remain largely unaffected. The hydroformylation was carried out as described in Example 4.

TABLE 2

Hydroformylation of MODE, parameters and experimental results

| Ligand | Substrate | Rh [ppm] | Ligand/ rhodium | Temp. [° C.] | Solvent | Pressure [bar] | Conversion [%] | n-Selectivity [%] |
|---|---|---|---|---|---|---|---|---|
| D-1 | MODE | 40 | 5 | 100 | Toluene | 50 | 82 | 95 |

In contrast, no uniform product was obtained when the comparative compound D-4 described in EP 0 472 071, which is not according to the invention, was used. A product mixture containing about 50% by mass of 9-methoxynon-7-enal was obtained. The phosphite according to the invention is thus significantly more selective than the comparative substance which is not according to the invention.

Example 6

Hydrolysis Stability 0.05 mol of the compound indicated in each case in Table 3 was in each case dissolved in 1 ml of $d_8$-toluene (Fluka) and a $^{31}$P-NMR spectrum was recorded. 18 mg of water (1 mmol, 20 equivalents) were subsequently added and the mixture was shaken vigorously for 1 minute. The mixture was allowed to stand at room temperature and a $^{31}$P-NMR spectrum was recorded firstly after 2 hours and then again after 6 days.

TABLE 3

Hydrolysis tests

| Ligand | Time [h] | $^{31}$P-NMR-spectroscopic purity of ligand |
|---|---|---|
| D-1 | 0 | >99% |
| D-1 | 2 | >99% |
| D-1 | 144 | >99% |
| D-2 | 0 | >95% |
| D-2 | 2 | >95% |
| D-2 | 144 | >95% |
| D-4 | 0 | >99% |
| D-4 | 2 | <5% |
| D-4 | 144 | <1%[a] |

[a]substance no longer detectable, complete decomposition

Table 3 shows that the phosphites according to the invention display a significantly increased hydrolysis stability compared to the comparative phosphite D-4 from EP 0 472 071, which is not according to the invention.

The invention claimed is:
1. A bisphosphite of formula I

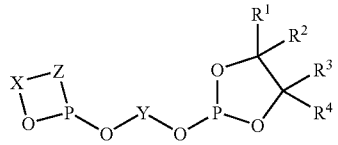

I wherein X is a divalent substituted or unsubstituted bisalkylene or bisarylene radical which may comprise one or more heteroatom(s), Y is a divalent substituted or unsubstituted bisarylene or bisalkylene radical which may comprise one or more heteroatom(s), Z is oxygen or $NR^9$, $R^1$, $R^2$, $R^3$, $R^4$ are identical or different, substituted or unsubstituted, unlinked aryl or heteroaryl radicals, and $R^9$ is hydrogen or a substituted or unsubstituted alkyl or aryl radical which may comprise one or more heteroatom(s).

2. The bisphosphite according to claim 1, wherein X is a radical Xa,

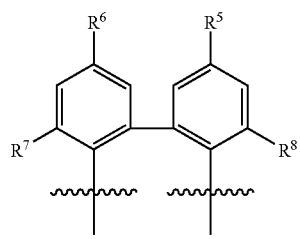

Xa where the radicals $R^5$, $R^6$, $R^7$, $R^8$ can be, independently of one another, substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms or H, F, Cl, Br, I, —$CF_3$, —$(CH_2)_i$ $(CF_2)_jCF_3$ where i=0-9 and j=0-9, —$SiR^{21}_3$, —$Si(OR^{21})_3$, —$SiR^{21}(OR^{21})_2$, —$SiR^{21}_2OR^{21}$, —$OSiR^{21}_3$, —$OSi(OR^{21})_3$, —$OSiR^{21}(OR^{21})_2$, —$OSiR^{21}_2OR^{21}$, —$OR^{19}$, —$COR^{19}$, —$CO_2R^{19}$, —$CO_2M$, —$SO_2R^{19}$, —$SOR^{19}$, —$SO_3R^{19}$, —$SO_3M$, —$SO_2NR^{19}R^{20}$, —$NR^{19}R^{20}$ or —$N=CR^{19}R^{20}$, wherein $R^{19}$, $R^{20}$ and $R^{21}$ are selected independently from the group consisting of H, monovalent substituted or unsubstituted aliphatic and aromatic hydrocarbon radicals having from 1 to 25 carbon atoms wherein $R^{21}$=H is excluded, and M is an alkali metal ion, formally half an alkaline earth metal ion, an ammonium ion or a phosphonium ion.

3. The bisphosphite according to claim 1, wherein X is an ethylene radical substituted by the radicals $R^{1'}$, $R^{2'}$, $R^{3'}$ and $R^{4'}$, wherein the radicals $R^{1'}$, $R^{2'}$, $R^{3'}$ and $R^{4'}$ have the same meaning as the radicals $R^1$, $R^2$, $R^3$, $R^4$.

4. The bisphosphite according to claim 3, wherein X is an ethylene radical substituted by the radicals $R^{1'}$, $R^{2'}$, $R^{3'}$ and $R^{4'}$, wherein the radicals $R^1$ and $R^{1'}$, $R^2$ and $R^{2'}$, $R^3$ and $R^{3'}$ and $R^4$ and $R^{4'}$ in each case are identical.

5. The bisphosphite according to claim 1, wherein the radicals $R^1$, $R^2$, $R^3$, $R^4$ are unsubstituted phenyl radicals.

6. The bisphosphite according to claim 1, wherein Y is selected from the group consisting of bisphenoxy radicals of formulae IIa to IId

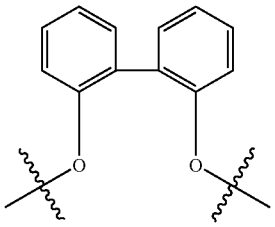

IIa

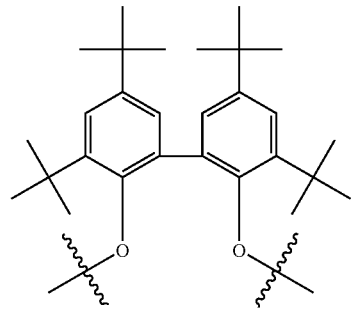

IIb

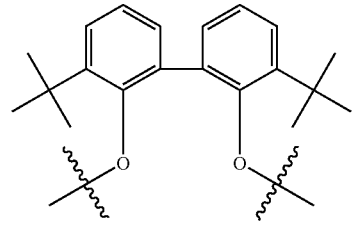

IIc

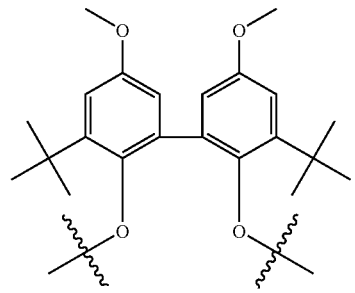

IId and bisnaphthoxy radicals of the formula III

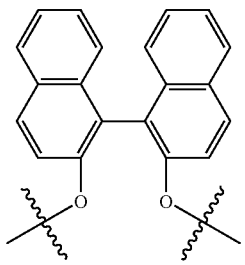

III

7. A phosphite-metal complex comprising a metal of Group 4, 5, 6, 7, 8, 9 or 10 of the Periodic Table of the Elements and one or more bisphosphites according to claim 1.

8. The phosphite-metal complex according to claim 7, wherein the metal is rhodium, palladium, nickel, platinum, cobalt or ruthenium.

9. In the method of hydroformylation, carbonylation, hydrogenation or hydrocyanation reaction, the improvement which comprises conducting said method with an active catalyst species comprising the bisphosphite according to claim 1.

10. The method according to claim 9, wherein the method is a homogeneous catalysis.

11. The method according to claim 9, wherein the method is the hydroformylation of olefins.

12. The method according to claim 11, wherein a metal complex having rhodium or cobalt as metal is used in hydroformylation.

13. The method according to claim 12, wherein the molar ratio of metal to bisphosphite in the reaction mixture is from 1:1 to 1:500.

14. A process for preparing a bisphosphite according to claim 1 comprising:
   1) reacting a diol Aa or an alcohol amine Ab with phosphorus trihalide to form an intermediate A;
   2) reacting a tetraarylethanediol Ca, which can bear identical or different, substituted or unsubstituted, linked or unlinked, fused or unfused aryl or heteroaryl radicals, with phosphorus trihalide to form an intermediate C;
   3) reacting the intermediate A or C with a diol Ba to form an intermediate B; and
   4) reacting the intermediate B with the intermediate A or C which was not used in process step 3).

15. The process according to claim 14, comprising reacting at least one of the diols Aa, Ba, Ca, the alcohol amine Ab, and the intermediate C in at least one of 1), 2), 3) and 4) with a metal compound to form the corresponding metal salt which is then reacted with the phosphorus trihalide.

16. The process according to claim 15, wherein sodium hydride, methyllithium or butyllithium is used as metal compound.

17. The process according to claim 14, comprising carrying out the reaction with phosphorus trihalide in the presence of a base.

18. The process according to claim 17, wherein a tertiary amine is used as base.

19. The bisphosphite according to claim 1, wherein the bisphosphite of formula I is selected from the group consisting of D-1, D-2, D-3 and Ib:

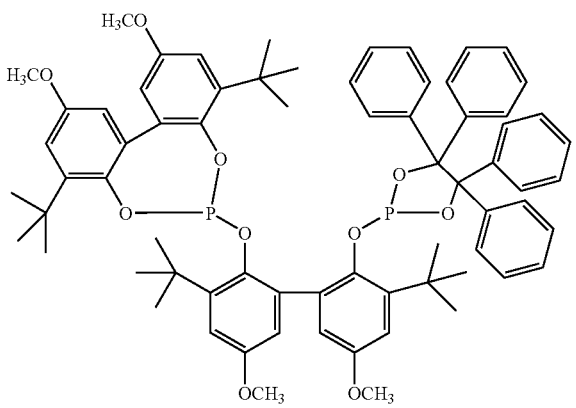

D-2

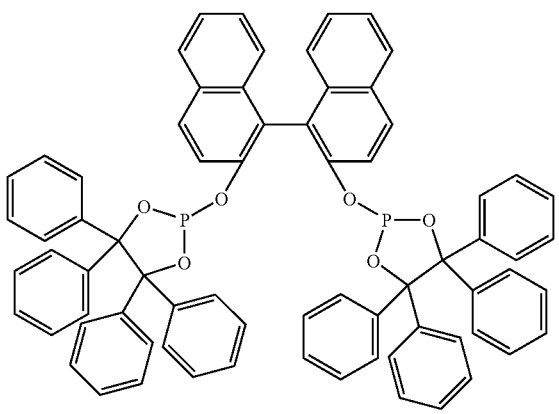

D-3

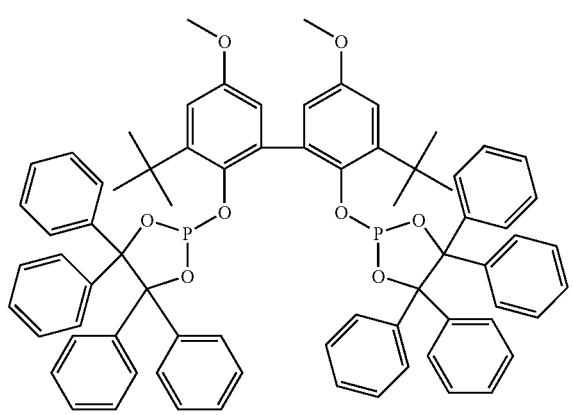

D-1

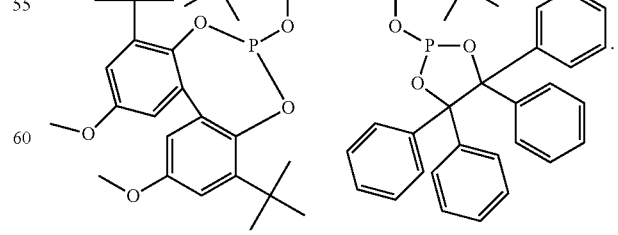

Ib

20. A bisphosphite selected from the group consisting of I-1, I-2 and I-3,

I-1

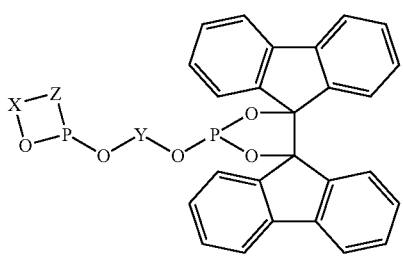

I-2

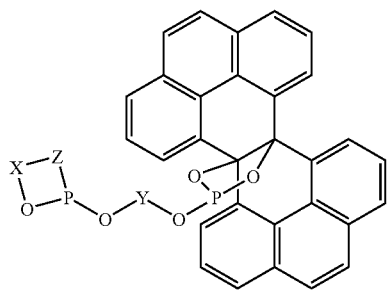

I-3

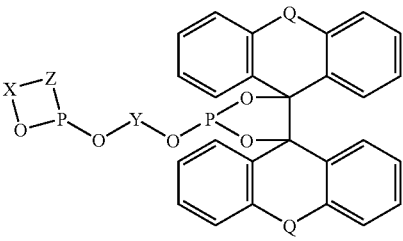

wherein X is a divalent substituted or unsubstituted bisalkylene or bisarylene radical which may comprise one or more heteroatom(s), Y is a divalent substituted or unsubstituted bisarylene or bisalkylene radical which may comprise one or more heteroatom(s), Z is oxygen or $NR^9$, $R^9$ is hydrogen or a substituted or unsubstituted alkyl or aryl radical which may comprise one or more heteroatom(s), the radicals Q are identical or different and are $CH_2$, $CR^9R^{10}$, $CHR^9$, O, NH or $NR^9$, where $R^9$ and $R^{10}$ are identical or different and have the meanings given above for $R^9$.

* * * * *